(12) United States Patent
Hess

(10) Patent No.: US 9,702,632 B2
(45) Date of Patent: Jul. 11, 2017

(54) APPARATUS AND METHOD FOR THE ANALYSIS OF GASES, IN PARTICULAR FOR THE ANALYSIS OF NATURAL GAS EXTRACTED AS SHALE GAS

(71) Applicant: Martin Hess, Ingolstadt (DE)

(72) Inventor: Martin Hess, Ingolstadt (DE)

( * ) Notice: Subject to any disclaimer, the term of this patent is extended or adjusted under 35 U.S.C. 154(b) by 869 days.

(21) Appl. No.: 14/079,683

(22) Filed: Nov. 14, 2013

(65) Prior Publication Data

US 2015/0129159 A1 May 14, 2015

(51) Int. Cl.
| | |
|---|---|
| E21B 43/00 | (2006.01) |
| F28D 15/00 | (2006.01) |
| G01N 33/22 | (2006.01) |
| E21B 36/00 | (2006.01) |
| F03G 7/04 | (2006.01) |
| E21B 43/34 | (2006.01) |
| E21B 43/24 | (2006.01) |

(52) U.S. Cl.
CPC ........... *F28D 15/00* (2013.01); *G01N 33/225* (2013.01); *E21B 36/00* (2013.01); *E21B 43/24* (2013.01); *E21B 43/34* (2013.01); *F03G 7/04* (2013.01)

(58) Field of Classification Search
CPC ... F28D 15/00; F28D 20/0039; G01N 33/225; G01N 33/00; G01N 33/241; G01N 21/3504; G01N 1/2294; G01N 1/22; F03G 7/04; E21B 43/00; E21B 43/34; E21B 36/00; E21B 43/24; Y10T 436/25875
USPC ........... 165/104.14, 11.1; 95/82; 436/24, 40; 73/863.11; 60/641.2, 641.3; 166/207, 166/302
See application file for complete search history.

(56) References Cited

U.S. PATENT DOCUMENTS

| | | | | |
|---|---|---|---|---|
| 2,386,832 A | * | 10/1945 | Zaikowsky | G01N 1/2294 166/254.2 |
| 2,437,045 A | * | 3/1948 | Roper | G01N 33/241 160/DIG. 13 |
| 3,578,080 A | * | 5/1971 | Closmann | E21B 43/2635 166/247 |
| 3,589,169 A | * | 6/1971 | Lafitte | G01N 25/142 23/294 R |
| 3,593,790 A | * | 7/1971 | Herce | C09K 8/592 166/267 |
| 3,714,811 A | * | 2/1973 | Daigle | E21B 7/185 436/30 |

(Continued)

*Primary Examiner* — Etsub Berhanu
*Assistant Examiner* — Jose O Class-Quinones
(74) *Attorney, Agent, or Firm* — Laurence A. Greenberg; Werner H. Stemer; Ralph E. Locher

(57) ABSTRACT

An apparatus and a method for the treating gases, such as natural gas extracted as shale gas, has a heat-insulated protective housing with a stratified liquid reservoir. An outer heat exchanger outside the protective housing has a primary side about which ambient air flows as heating medium and a secondary side for cold stratified reservoir liquid to be heated and fed back to the stratified reservoir. A defined quantity of gas flows through an inner heat exchanger inside the housing and is heated to a defined gas temperature by heated stratified reservoir liquid. The cooled stratified reservoir liquid leaving the inner heat exchanger feeds back to the stratified reservoir. The heated gas leaving the inner heat exchanger flows to a gas analysis apparatus inside or outside the heat-insulated protective housing.

20 Claims, 1 Drawing Sheet

(56) References Cited

U.S. PATENT DOCUMENTS

| | | | | |
|---|---|---|---|---|
| 4,130,474 A | * | 12/1978 | Anthony | C10G 1/04 208/435 |
| RE33,678 E | * | 9/1991 | Campbell | B01D 53/22 95/39 |
| 6,907,923 B2 | * | 6/2005 | Sienel | F24D 17/02 122/437 |
| 7,004,231 B2 | * | 2/2006 | Yang | F24J 3/06 165/11.1 |
| 2005/0016198 A1 | * | 1/2005 | Wowk | A01N 1/02 62/371 |
| 2010/0162791 A1 | * | 7/2010 | Breviere | G01N 1/40 73/23.31 |
| 2011/0226440 A1 | * | 9/2011 | Bissell | F28D 20/0039 165/10 |

* cited by examiner

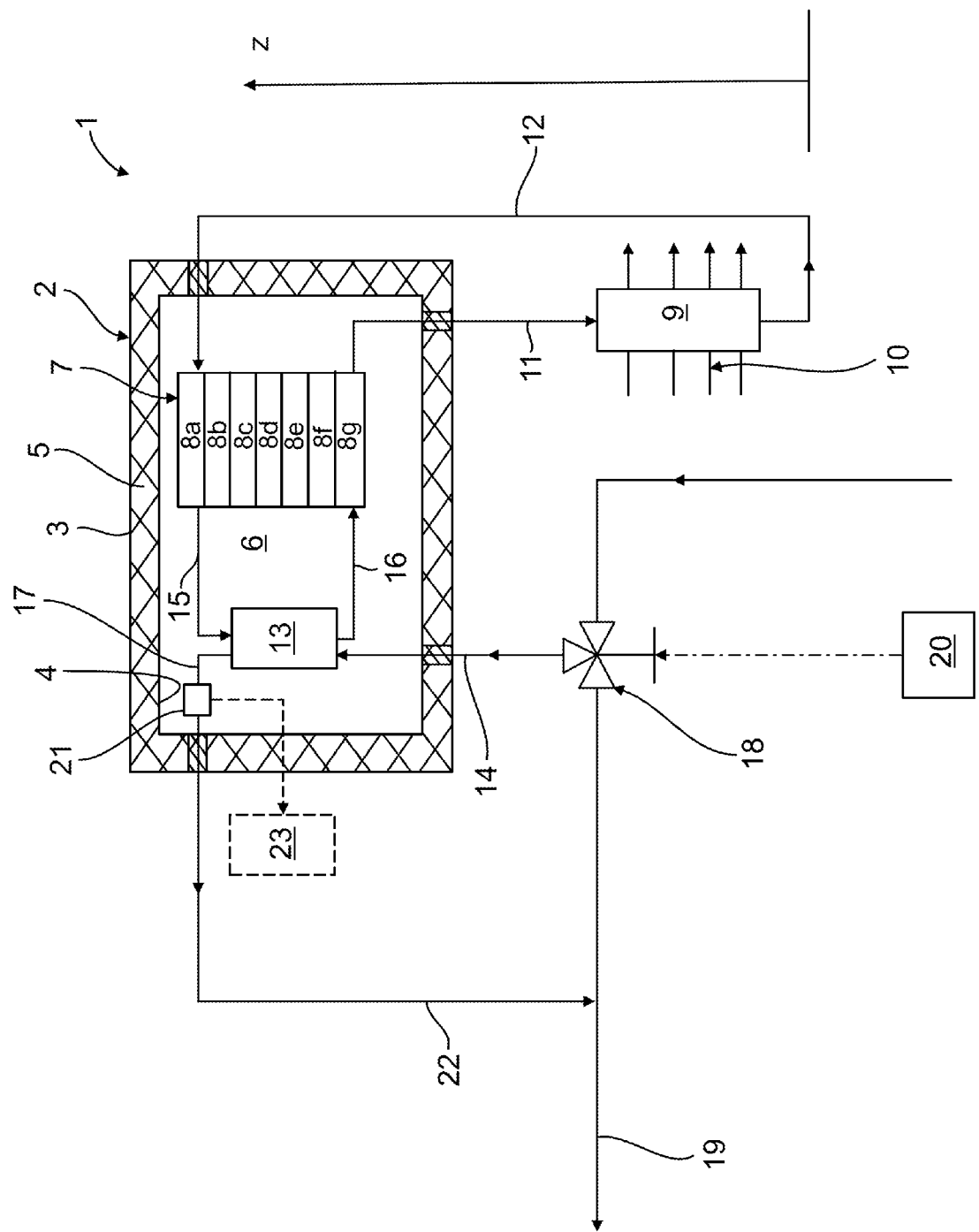

APPARATUS AND METHOD FOR THE ANALYSIS OF GASES, IN PARTICULAR FOR THE ANALYSIS OF NATURAL GAS EXTRACTED AS SHALE GAS

BACKGROUND OF THE INVENTION

Field of the Invention

The invention relates to an apparatus for the analysis of gases, in particular for the analysis of natural gases that are extracted as shale gases, and to a method for the analysis of gases, in particular for the analysis of natural gases extracted as shale gases.

Where energy-generating raw materials are concerned, it is customary to distinguish between conventional and nonconventional deposits. A conventional deposit is referred to when classic methods for development and extraction are adopted, while nonconventional deposits have to be developed by way of alternative techniques. In addition to petroleum and coal as energy-generating raw materials, in particular, natural gas also plays a major part. Natural gas from a nonconventional deposit does not flow into the extraction well without further outlay in technical terms, because either it is not present as a free gas phase in the rock or the reservoir rock is not sufficiently permeable. Shale gas, for example, is a nonconventional natural gas of this kind, in which the natural gas is stored in so-called claystone formations. Claystone occurs when fine-grained mineral components settle in the depths of bodies of water where flow is insignificant. Thus, organic material, such as, for example, algae, falls to the bottom and may be included in the sediment as a result of the settlement of further mineral components. Over millions of years, massive sediment stacks arise in this way, which are compressed by the pressure of the rocks lying on them and are designated as claystones or shale. Subsidence causes claystone to infiltrate into depths which have increased temperatures. The temperature rise initially causes the organic material contained there to give rise predominantly to petroleum. Natural gas is also formed later, and petroleum which has already occurred may be transformed into natural gas. Such claystones are designated as parent rocks. Some of the hydrocarbons formed may escape from these parent rocks and fill conventional deposits. The hydrocarbons remaining in the claystones are designated correspondingly as shale oil or shale gas which must or can be extracted by way of nonconventional extraction methods.

The extraction of shale gas is carried out by so-called fracking (i.e., induced hydraulic fracturing, hydrofracturing), in which, during the drilling work, a borehole is partially sealed off by the use of steel pipes. The interspace between the borehole wall and the outside of the pipes is sealed off with cement, in order to anchor the pipes firmly in the rock and prevent liquids or gases from overflowing into overhead strata via the annular space. Only when a borehole secured in this way is made can a fracking measure be carried out, in which a liquid is pressed into the deep well in order to generate in the reservoir rock cracks via which the shale gas can then ultimately escape and be extracted.

These shale gases extracted in this way have a relatively high moisture content, and therefore, under the changeable temperature conditions usually prevailing in the drilling zones, there is a risk that specific constituents of the extracted shale gas condense and, for example, crystallize out together with the salts or salt hydrates dissolved in them. This may then lead, in turn, to the contamination and fouling of lines and instruments, which, overall, may have an adverse effect upon their operating and functioning capacity. Furthermore, when gas analyses are carried out, there is the risk that, for example because gas components condense or crystallize out, the gas composition in the region upstream of the gas analyzers changes, thus ultimately leading to a falsified measurement result.

SUMMARY OF THE INVENTION

It is accordingly an object of the invention to provide an apparatus and a method for the analysis of gases, in particular for the analysis of shale gas, which overcome the above-mentioned disadvantages of the heretofore-known devices and methods of this general type and which leads to gas analysis with high measurement quality and therefore with high functional reliability.

With the foregoing and other objects in view there is provided, in accordance with the invention, an apparatus for the treatment of gases, in particular natural gas extracted as shale gas. The novel apparatus comprising:

a heat-insulated protective housing;

a stratified reservoir disposed in said heat-insulated protective housing and configured for accommodating and storing therein a stratified reservoir liquid in superposed layers in a plurality of temperature zones having mutually different temperatures and including a cold temperature zone and a high temperature zone;

an outer heat exchanger disposed outside said heat-insulated protective housing and fluidically communicating with said stratified reservoir through a stratified reservoir liquid branch line connected to said cold temperature zone of said stratified reservoir, wherein ambient air flows around said outer heat exchanger as a heating medium for heating a defined quantity of cold stratified reservoir liquid drawn off from said cold temperature zone of said stratified reservoir, and wherein the cold stratified reservoir liquid, which has a lower temperature than the ambient air, is heated by heat exchange with the ambient air to form a hot stratified reservoir liquid at a defined stratified reservoir liquid temperature;

a stratified reservoir liquid metering line disposed to conduct the hot stratified reservoir liquid from said outer heat exchanger back to said stratified reservoir into said high temperature zone;

an inner heat exchanger disposed inside said heat-insulated protective housing and conducting therethrough a defined quantity of a gas to be heated, received from a gas feed line, and a defined quantity of hot stratified reservoir liquid drawn off from said high temperature zone of said stratified reservoir, received through a stratified reservoir liquid feed line, wherein the gas, which has a lower temperature than the hot stratified reservoir liquid, is heated to form heated gas at a defined gas temperature while the hot stratified reservoir liquid is cooled to form cooled stratified reservoir liquid;

a stratified reservoir liquid recirculation line connected to conduct the cooled stratified reservoir liquid from said inner heat exchanger to said stratified reservoir into said cold temperature zone, and a gas discharge line connected to conduct the heated gas away from said inner heat exchanger; and a gas analysis apparatus connected to receive the heated gas from said gas discharge line.

In other words, according to the invention, an apparatus and a method for the treatment of gases, in particular of natural gases extracted as shale gases, are proposed, in which a heat-insulated protective housing is provided, a stratified reservoir for a stratified reservoir liquid being arranged in the protective housing. A suitable stratified reservoir liquid is, in particular, water. This stratified reservoir liquid is accommodated and stored in the stratified reservoir in superposed layers in a plurality of temperature zones having a different temperature. In actual fact, for this purpose, the different density of the water at different temperatures is utilized in order to store the water in superposed layers in these different temperature zones.

Outside the heat-insulated protective housing, an outer heat exchanger is arranged, around or through which, on the one hand, ambient air flows as heating medium (and which, if appropriate, is additionally heated by solar radiation), and through which, on the other hand, flows a defined quantity of a cold stratified reservoir liquid which is fed to the outer heat exchanger and which is drawn off by means of a stratified reservoir liquid branch line from a cold temperature zone of the stratified reservoir and is routed outside the heat-insulated protective housing to the outer heat exchanger. The cold stratified reservoir liquid, which has a lower temperature than the ambient air, is then heated by heat exchange with the ambient air to a defined stratified reservoir liquid temperature, so that the stratified reservoir liquid leaving the outer heat exchanger can then be routed back to the stratified reservoir again by means of a stratified reservoir liquid metering line and be stored there in a corresponding high temperature zone.

Furthermore, according to the invention, an inner heat exchanger is provided, which is accommodated in the heat-insulated protective housing and through which, on the one hand, flows a defined quantity of a gas to be heated, fed to the inner heat exchanger by means of a gas feed line, and through which, on the other hand, flows a defined quantity of a hot stratified reservoir liquid drawn off from the inner heat exchanger out of a high temperature zone for the stratified reservoir by means of a stratified reservoir liquid feed line. As a result, the gas to be heated, which has a lower temperature than the hot stratified reservoir liquid, is heated to a defined stipulated gas temperature, while the hot stratified reservoir liquid is cooled. Preferably, the gas is heated to a gas temperature which is higher than the condensation temperature of at least one defined gas component of the gas to be heated. The inner heat exchanger is preferably a heat exchanger in which the media which are in heat exchange with one another have no direct contact with one another, as is the case, for example, with regard to a plate heat exchanger or to a tube bundle heat exchanger.

Subsequently, the cooled stratified reservoir liquid leaving the inner heat exchanger can then be routed back to the stratified reservoir again by means of a stratified reservoir liquid recirculation line and be stored there in a corresponding cold temperature zone, while the heated gas likewise leaving the inner heat exchanger is fed by means of a gas discharge line to a gas analysis apparatus which may be arranged outside or inside the heat-insulated protective housing.

Such an apparatus and method management according to the invention ensure in a simple way that the gas quantity to be analyzed, in particular shale gas which is extracted by means of fracking, does not cool undesirably in the run-up to gas analysis in such a way that specific components of the gas may condense and salts or salt hydrates may undesirably crystallize out, thus falsifying in an undesirable way the measurement and/or analysis result obtained or determined by means of the gas analysis apparatus. Instead, by means of the apparatus and method management according to the invention, the undershooting of a dew point is reliably avoided, thus ensuring that the analyzed gas has a gas composition which corresponds exactly to the composition of the gas actually extracted. The gas heating or gas drying provided according to the invention can, moreover, be carried out advantageously in energy terms, in particular by utilizing natural convection, this being explained in more detail below. The apparatus according to the invention and the method management according to the invention are consequently also especially suitable, in particular, for those applications or places of use where there is no power supply or an insufficient power supply for operating drying plants, as is the case, for example, along pipelines which run in remote areas.

Especially preferably, the inner heat exchanger is designed at the same time as a pressure reducer, by means of which the gas pressure can be lowered to a desired gas pressure. This, too, counteracts condensation and therefore helps to ensure that the gas is fed in the desired composition to the gas analysis apparatus.

If, according to an especially preferred refinement of the present invention, the outer heat exchanger is arranged geodetically lower than the stratified reservoir, that is to say is arranged below the stratified reservoir, as seen in the direction of the vertical axis, then, at all those ambient air temperatures which are higher than the temperature of the stratified reservoir liquid in at least one cold temperature zone of the stratified reservoir, cold stratified reservoir liquid can flow by natural convection via the stratified reservoir liquid discharge line to the outer heat exchanger, while the reservoir liquid heated by the outer heat exchanger rises or flows via the stratified reservoir metering line toward the stratified reservoir. An essentially energy-free or extremely low-energy apparatus and method management can consequently advantageously be achieved merely by utilizing natural convection.

In principle, however, there is also the possibility of providing a control and/or regulating device which is operated by energy, as may take place, for example, via solar cells or the like, but which, in principle, may, of course, also be fed with current in any other, in particular conventional way. By means of a control and/or regulating device of this kind, throttle and/or shut-off members and/or conveying devices can be activated and/or regulated, for example as a function of the nature and/or composition of the gas to be heated, in particular as a function of the content of condensate-forming hydrocarbons, such that a gas quantity feedable to the inner heat exchanger by means of the gas feed line and/or a stratified reservoir liquid quantity feedable to the inner heat exchanger by means of the stratified reservoir liquid feed line and/or a temperature zone, out of which the hot stratified reservoir liquid is to be drawn off, are/is consequently stipulated such that the gas to be heated is heated to the desired gas temperature. As stated above, here the gas is preferably heated to a gas temperature which is higher than the condensation temperature of at least one defined gas component of the gas to be heated. Particularly in connection with shale gas as the gas to be treated or to be heated, it is advantageous that the gas is heated to a temperature of at least 20° C. (degrees Celsius), preferably to a temperature of 20° C. up to and including 30° C.

The gas leaving the gas analysis apparatus is preferably recirculated by means of a draw-off line of a main gas line, for example a pipeline, from which the gas feed line leading to the inner heat exchanger has branched off the gas quantity to be fed to the inner heat exchanger and to be heated and analyzed.

The heat-insulated protective housing may, in principle, be constructed differently. A set-up of the heat-insulated protective housing is especially preferred in which at least its outer walls are produced from a glass fiber-reinforced plastic material as a sandwich element with an outer skin and with an inner skin spaced apart from the latter, at least one heat-insulating layer and/or one fire protection layer being arranged and accommodated in the region between the outer skin and the inner skin. By means of a heat-insulated protective housing of this kind, an especially lightweight set-up is made available which can be produced in a simple way. Moreover, because of the low weight, protective housings of this kind have the advantage that they can be erected in and on buildings and/or steel structures. Furthermore, protective housings of this kind are fully transportable and can be ready-equipped, for example provided with the appropriate installations, at the factory. Protective housings of this kind acquire their strength from the geometric moment of inertia, high stresses being absorbed in the stable outer skin and the stable inner skin.

Other features which are considered as characteristic for the invention are set forth in the appended claims.

Although the invention is illustrated and described herein as embodied in an apparatus and method for the analysis of gases, in particular for the analysis of natural gases extracted as shale gases, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawing FIGURE.

BRIEF DESCRIPTION OF THE DRAWING

The sole FIGURE is a diagrammatic view of an apparatus according to the invention for the treatment of gases, for example of natural gases extracted as shale gases by means of fracking.

DETAILED DESCRIPTION OF THE INVENTION

Referring now to the sole FIGURE of the drawing in detail, the apparatus 1 according to the invention has a heat-insulated protective housing 2. The latter is illustrated merely highly diagrammatically and by way of example, for example, as being erected on a load-bearing stand and/or a steel structure. The protective housing 2 or its outer walls are designed as a sandwich element and are composed of a stable outer skin 3 and of a stable inner skin 4 spaced apart from the latter, both made from a glass fiber-reinforced plastic material, a heat-insulating layer 5, which may at the same time also form a fire protection layer, being arranged and accommodated in the intermediate space between the outer skin 3 and the inner skin 4.

A stratified reservoir 7 for, for example, water as stratified reservoir liquid is arranged in the inner space 6 of the heat-insulated protective housing 2, the stratified reservoir liquid being accommodated and stored in the stratified reservoir 7 in superposed layers in a plurality of temperature zones 8a to 8g having different temperatures. The temperature of these individual temperature zones 8a to 8g increases from below (as seen in the direction of the vertical axis z), so that the temperature zone 8g has the lowest temperature, while the uppermost temperature zone 8a forms the temperature zone with the highest water temperature. For example, the temperature zones 8a and 8b and, if appropriate, also 8a to 8c may form a high temperature zone, while the temperature zones 8f and 8g, if appropriate also the temperature zones 8e to 8g, may form a low or cold temperature zone. This ultimately depends upon the fraction of cold water and of hot water in the stratified reservoir 7.

Further, the apparatus 1 according to the invention comprises an outer, or external heat exchanger 9 which is arranged outside the heat-insulated protective housing 2 and around or through which, on the one hand, ambient air 10 flows, forming a heating medium, and which, if appropriate, is additionally heated by solar radiation, and through which, on the other hand, flows a defined quantity of a cold stratified reservoir liquid which is fed to the outer heat exchanger and which is drawn off from the cold temperature zone 8g of the stratified reservoir 7 by means of a branch line 11 and is routed outside the protective housing 2 to the outer heat exchanger 9.

This external heat exchanger 9 lies below the stratified reservoir 7, as seen in the direction of the vertical axis z, and is therefore arranged geodetically lower than the latter, so that, at those ambient air temperatures which are higher than the temperature of the stratified reservoir liquid in at least the cold temperature zone 8g, cold stratified reservoir liquid or cold water flows via the branch line 11 to the outer heat exchanger 9 by virtue of natural convection, while the reservoir liquid heated by the outer heat exchanger 9 flows back or rises as hot water via a metering line 12 to the stratified reservoir 7 and is stored there, for example, in the high temperature zone 8a.

Thus, in summary, the cold water which is drawn off out of the cold temperature zone 8g and has a lower temperature than the ambient air 10 is heated by heat exchange with the latter to a defined hot water temperature, thus always ensuring that sufficient hot water for the gas heating explained in more detail below is available in the stratified reservoir 7.

Furthermore, in the heat-insulated protective housing 2, an inner or internal heat exchanger 13 is arranged, through which, on the one hand, a defined quantity of a gas to be heated, fed to the inner heat exchanger 13 by way of a gas feed line 14, flows and through which, on the other hand, flows a defined quantity of hot water which is fed to the inner heat exchanger 13 by means of a stratified reservoir liquid feed line 15 and is drawn off out of the high temperature zone 8a of the stratified reservoir 7. As a result, the gas to be heated, which has a lower temperature than the drawn-off hot water, is heated, while the hot water is cooled, to a desired defined gas temperature, for example is heated to a gas temperature which is higher than the condensation temperature of at least one defined gas component of the gas to be heated. The inner heat exchanger 13 is at the same time designed as a pressure reducer, so that, by means of this, a reduction in gas pressure can also take place in the run-up to the feed of the heated gas to a gas analysis apparatus 21.

The cooled stratified reservoir liquid leaving the inner heat exchanger 13 is then routed back again, inside the protective housing 2, by means of a stratified reservoir liquid recirculation line 16 to the stratified reservoir 7 and is stored there, for example, in the corresponding cold temperature zone, for example the cold temperature zone 8g. The heated gas likewise leaving the inner heat exchanger 13 is then fed by way of a gas discharge line 17 to the gas analysis apparatus 21 which is preferably likewise arranged in the heat-insulated protective housing 2. The gas leaving the gas analysis apparatus 21 is then routed outside the heat-insulated protective housing 2 by way of a draw-off line 22.

Alternatively to this, however, the gas analysis apparatus 21 could also be arranged outside the protective housing 2, but in this case the transport distance should be very short here, for example the gas analysis apparatus should be arranged directly following or adjoining the protective housing 2, in order to avoid gas cooling. Alternatively or additionally, if a gas analysis apparatus is arranged outside the protective housing in this way, there could also be provision for coupling the outward-routed gas line to a hot water line in a heat-transmitting manner, in which case the hot water could then be drawn off from the stratified reservoir here. However, the latter embodiment is not shown in any more detail here.

All the leadthroughs of lines through the housing wall of the protective housing 2 are preferably made leaktight.

As may also be gathered from the single FIGURE, the gas feed line 14 may be branched off from a gas-carrying pipeline 19, for example by means of a valve device 18, and be fed to the inner heat exchanger 13, so that the gas is subsequently recirculated into the pipeline 19 again via the draw-off line 22. Alternatively to this, the gas feed line 14 and therefore also the draw-off line 22 could not even be provided, however, and the apparatus could, for example, be integrated directly into the pipeline 19, although this is not illustrated here.

Furthermore, if appropriate, a control and/or regulating (i.e., closed-loop control) device 20 may be provided, by means of which throttle and/or shut-off members and/or conveying devices, which may possibly be present, are activated and/or regulated, in particular as a function of the nature or composition of the gas to be heated, in particular as a function of the content of condensate-forming hydrocarbons, such that a gas quantity feedable to the inner heat exchanger 13 by means of the gas feed line 14 and/or a stratified reservoir liquid quantity feedable to the inner heat exchanger 13 by means of the stratified reservoir liquid feed line 15 and/or a temperature zone, out of which the hot stratified reservoir liquid is to be drawn off, are/is consequently stipulated such that the gas to be heated is heated to the desired gas temperature, preferably in such a way that the gas is heated to a gas temperature which is higher than the condensation temperature of at least one defined gas component of the gas to be heated. However, this is illustrated in the FIGURE merely by way of example and highly diagrammatically by the signal line which is routed to the valve device 18.

The gas analysis apparatus 21 may, in principle, be formed by any suitable gas analyzer, by means of which the composition, temperature, pressure, etc. of the gas to be analyzed can be measured and determined. The measurement and analysis results of the gas analysis apparatus 21 can then be fed to any evaluation device 23 arranged outside the protective housing 2, as is illustrated merely highly diagrammatically and by dashes in the single FIGURE.

The invention claimed is:

1. An apparatus for the treatment of gases, the apparatus comprising:
   a heat-insulated protective housing;
   a stratified reservoir disposed in said heat-insulated protective housing and configured for accommodating and storing therein a stratified reservoir liquid in superposed layers in a plurality of temperature zones having mutually different temperatures and including a cold temperature zone and a high temperature zone;
   an outer heat exchanger disposed outside said heat-insulated protective housing and fluidically communicating with said stratified reservoir through a stratified reservoir liquid branch line connected to said cold temperature zone of said stratified reservoir, wherein ambient air flows around said outer heat exchanger as a heating medium for heating a defined quantity of cold stratified reservoir liquid drawn off from said cold temperature zone of said stratified reservoir, and wherein the cold stratified reservoir liquid, which has a lower temperature than the ambient air, is heated by heat exchange with the ambient air to form a hot stratified reservoir liquid at a defined stratified reservoir liquid temperature;
   a stratified reservoir liquid metering line disposed to conduct the hot stratified reservoir liquid from said outer heat exchanger back to said stratified reservoir into said high temperature zone;
   an inner heat exchanger disposed inside said heat-insulated protective housing and conducting therethrough a defined quantity of a gas to be heated, received from a gas feed line, and a defined quantity of hot stratified reservoir liquid drawn off from said high temperature zone of said stratified reservoir, received through a stratified reservoir liquid feed line, wherein the gas, which has a lower temperature than the hot stratified reservoir liquid, is heated to form heated gas at a defined gas temperature while the hot stratified reservoir liquid is cooled to form cooled stratified reservoir liquid;
   a stratified reservoir liquid recirculation line connected to conduct the cooled stratified reservoir liquid from said inner heat exchanger to said stratified reservoir into said cold temperature zone, and a gas discharge line connected to conduct the heated gas away from said inner heat exchanger; and
   a gas analysis apparatus connected to said gas discharge line for receiving the heated gas.

2. The apparatus according to claim 1, wherein said inner heat exchanger is configured to also act as a pressure reducer lowering a gas pressure to a stipulated pressure value.

3. The apparatus according to claim 1, wherein said inner heat exchanger is configured to heat the gas to a gas temperature that is higher than a condensation temperature of at least one defined gas component of the gas to be heated.

4. The apparatus according to claim 1, wherein said outer heat exchanger is disposed geodetically lower than said stratified reservoir, so that, at those ambient air temperatures which are higher than the temperature of the stratified reservoir liquid in at least one cold temperature zone of said stratified reservoir, cold stratified reservoir liquid flows via said stratified reservoir liquid branch line to said outer heat exchanger by natural convection, while the reservoir liquid heated by said outer heat exchanger flows via said stratified reservoir liquid metering line to the stratified reservoir.

5. The apparatus according to claim 1, which comprises at least one control device configured to selectively activate throttle and/or shut-off members as a function of a nature and a composition of the gas to be heated, such that a gas quantity feedable to the inner heat exchanger by way of said gas feed line and/or a stratified reservoir liquid quantity feedable to said inner heat exchanger by way of said stratified reservoir liquid feed line and/or a temperature zone, out of which the hot stratified reservoir liquid is to be drawn off, are/is stipulated such that the gas to be heated is heated to the desired gas temperature.

6. The apparatus according to claim 5, wherein said control device is an open controller or a closed-loop control device configured to activate based on a content of condensate-forming hydrocarbons in the gas to be heated, and the gas is heated to a gas temperature which is higher than a condensation temperature of at least one defined gas component of the gas to be heated.

7. The apparatus according to claim 1, wherein said heat-insulated protective housing has outer walls of glass fiber-reinforced plastic material as a sandwich element with an outer skin and with an inner skin spaced apart from said outer skin, and at least one heat-insulating layer and/or fire protection layer disposed between said outer skin and said inner skin.

8. The apparatus according to claim 1, wherein the stratified reservoir liquid is water.

9. The apparatus according to claim 1, which further comprises a draw-off line connected between said gas analysis apparatus and a main gas line, and wherein said gas feed line leading to said inner heat exchanger branches off from the main gas line to feed a gas quantity to said inner heat exchanger for heating and analysis.

10. A method for the treatment of gases, the method which comprises:
providing an analysis apparatus with:
a heat-insulated protective housing;
a stratified reservoir, arranged in the heat-insulated protective housing, for a stratified reservoir liquid, the stratified reservoir liquid being accommodated and stored in the stratified reservoir in superposed layers in a plurality of temperature zones having mutually different temperatures;
an outer heat exchanger arranged outside the heat-insulated protective housing and around and/or through which, on the one hand, ambient air flows as heating medium and through which, on the other hand, flows a defined quantity of a cold stratified reservoir liquid which is fed to the outer heat exchanger and which is drawn off from a cold temperature zone of the stratified reservoir by way of a stratified reservoir liquid branch line and is routed outside the protective housing to the outer heat exchanger, in such a way that the cold stratified reservoir liquid, which has a lower temperature than the ambient air, is heated by heat exchange with the ambient air to a defined stratified reservoir liquid temperature; and
a stratified reservoir liquid metering line for routing the heated stratified reservoir liquid leaving the outer heat exchanger back to the stratified reservoir for storage in a corresponding high temperature zone of the stratified reservoir;
providing an inner heat exchanger in the heat-insulated protective housing and conducting a defined quantity of a gas to be heated through a gas feed line and through the inner heat exchanger and conducting a defined quantity of a hot stratified reservoir liquid drawn off from a high temperature zone of the stratified reservoir by way of a stratified reservoir liquid feed line through the inner heat exchanger, to thereby heat the gas from a lower temperature than the hot stratified reservoir liquid to a defined gas temperature while cooling the hot stratified reservoir liquid; and
routing the cooled stratified reservoir liquid leaving the inner heat exchanger back by way of a stratified reservoir liquid recirculation line to the stratified reservoir and storing the cooled stratified reservoir liquid there in a corresponding cold temperature zone, while the heated gas likewise leaving the inner heat exchanger is fed through a gas discharge line to a gas analysis apparatus arranged inside or outside the heat-insulated protective housing.

11. The method according to claim 10, which comprises providing natural gas extracted as shale gases for analysis in the analysis apparatus.

12. The method according to claim 10, wherein the inner heat exchanger is also configured as a pressure reducer, by way of which the gas pressure is lowered to a stipulated pressure value.

13. The method according to claim 10, which comprises heating the gas in the inner heat exchanger to a gas temperature that is higher than a condensation temperature of at least one defined gas component of the gas to be heated.

14. The method according to claim 10, which comprises placing the outer heat exchanger at a position that is geodetically lower than the stratified reservoir, so that, at those ambient air temperatures which are higher than the temperature of the stratified reservoir liquid in at least one cold temperature zone of the stratified reservoir, cold stratified reservoir liquid flows via the stratified reservoir liquid branch line to the outer heat exchanger by natural convection, while the reservoir liquid heated by the outer heat exchanger flows via the stratified reservoir liquid metering line to the stratified reservoir.

15. The method according to claim 10, which further comprises providing at least one control device and activating and/or regulating therewith throttle and/or shut-off members as a function of a nature and/or composition of the gas to be heated, such that a gas quantity feedable to the inner heat exchanger by way of the gas feed line and/or a stratified reservoir liquid quantity feedable to the inner heat exchanger by way of the stratified reservoir liquid feed line and/or a temperature zone, out of which the hot stratified reservoir liquid is to be drawn off, are/is stipulated such that the gas to be heated is heated to the desired gas temperature.

16. The method according to claim 15, wherein the control device is an open controller or a closed-loop control device carrying out the activating step based on a content of condensate-forming hydrocarbons in the gas to be heated, and heating the gas to a gas temperature that is higher than a condensation temperature of at least one defined gas component of the gas to be heated.

17. The method according to claim 10, which comprises heating the gas to a temperature of at least 20° C.

18. The method according to claim 17, which comprises heating the gas to a temperature of up to and including 30° C.

19. The method according to claim 10, wherein the stratified reservoir liquid is water.

20. The method according to claim 10, which comprises feeding the gas leaving the gas analysis apparatus by way of a draw-off line to a main gas line, from which the gas feed line leading to the inner heat exchanger branches off a gas quantity and feeds the gas to the inner heat exchanger for heating and subsequent analysis.

* * * * *